United States Patent
Bitter (12)

(10) Patent No.: US 9,927,357 B2
(45) Date of Patent: Mar. 27, 2018

(54) PROCESS GAS ANALYZER AND METHOD FOR ANALYZING A PROCESS GAS

(71) Applicant: Siemens Aktiengesellschaft, Munich (DE)

(72) Inventor: Ralf Bitter, Karlsruhe (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 15/176,367

(22) Filed: Jun. 8, 2016

(65) Prior Publication Data

US 2016/0363530 A1 Dec. 15, 2016

(30) Foreign Application Priority Data

Jun. 12, 2015 (EP) .................................... 15171901

(51) Int. Cl.
| | |
|---|---|
| *G01N 21/39* | (2006.01) |
| *G01N 21/27* | (2006.01) |
| *G01N 21/3504* | (2014.01) |
| *G01N 21/15* | (2006.01) |

(Continued)

(52) U.S. Cl.
CPC ............ *G01N 21/39* (2013.01); *G01N 21/15* (2013.01); *G01N 21/274* (2013.01); *G01N 21/3504* (2013.01); *G01N 21/85* (2013.01); *G01N 33/0026* (2013.01); *G01N 2021/151* (2013.01); *G01N 2021/8578* (2013.01); *G01N 2201/06113* (2013.01); *G01N 2201/127* (2013.01)

(58) Field of Classification Search
CPC .. G01N 21/39; G01N 21/274; G01N 21/3504; G01N 21/15; G01N 21/85; G01N 2201/06113; G01N 2201/127; G01N 2021/151

See application file for complete search history.

(56) References Cited

U.S. PATENT DOCUMENTS 3,731,530 A * 5/1973 Tanguy ................. E21B 21/067
73/152.42
5,337,289 A * 8/1994 Fasching ............. G01F 23/2962
340/612

(Continued)

FOREIGN PATENT DOCUMENTS

| DE | 102012223874 | 5/2014 |
|---|---|---|
| DE | 102013213730 | 1/2015 |
| EP | 1 693 665 | 8/2016 |

*Primary Examiner* — Sang Nguyen
(74) *Attorney, Agent, or Firm* — Cozen O'Connor

(57) ABSTRACT

A process gas analyzer and method for analyzing a process gas carried in a plant section, wherein light from a light source is passed through the process gas and detected via a detector, evaluated in an evaluation unit to produce an analysis result with respect to the absorption in the process gas, where chambers or purging pipes, present between the light source and the plant section and also between the detector and the plant section, are flushed with a purge gas to analyze the process gas, and where the volume flow rate of the purge gas is periodically modulated and the effect of the purge gas on the analysis result is determined based on changes in the detected absorption caused by the modulation and removed from the analysis result to enable a high degree of compensation for measurement errors caused by the purging.

16 Claims, 3 Drawing Sheets

(51) Int. Cl.
    *G01N 21/85*         (2006.01)
    *G01N 33/00*         (2006.01)

(56) References Cited

U.S. PATENT DOCUMENTS

| | | | | |
|---|---|---|---|---|
| 5,621,213 | A * | 4/1997 | Barshad | G01N 21/33 250/252.1 |
| 5,747,809 | A * | 5/1998 | Eckstrom | G01N 21/3504 250/339.13 |
| 6,425,252 | B1 * | 7/2002 | Kobayashi | F17C 13/002 62/292 |
| 2006/0192967 | A1 | 8/2006 | Kluczynski | |
| 2012/0236323 | A1 | 9/2012 | Kuoppa | |
| 2012/0283961 | A1 * | 11/2012 | Wittmann | G01N 21/39 702/24 |
| 2014/0185035 | A1 | 7/2014 | Depenheuer et al. | |
| 2015/0077754 | A1 | 3/2015 | Schumann et al. | |
| 2015/0089993 | A1 * | 4/2015 | Bitter | G01J 3/28 73/1.06 |

* cited by examiner

PROCESS GAS ANALYZER AND METHOD FOR ANALYZING A PROCESS GAS

BACKGROUND OF THE INVENTION

1. Field of the Invention

The Invention relates to gas analyzers and, more particularly, to a process gas analyzer and method for analyzing a process gas carried in a plant section.

2. Description of the Related Art

US 2012/0236323 A1 discloses a method and a process gas analyzer.

In the case of gas analyzers operating in accordance with the transmitted light method, the light from a light source is guided through a gas to be analyzed and subsequently detected. The light can be generated wavelength selectively and detected in broadband fashion (laser spectrometer, for example), or it can be generated in broadband fashion and detected wavelength selectively (nondispersive infrared (NDIR) gas analyzer, for example). In the case of in-situ process gas analyzers, such as those known from US 2012/0236323 A1, DE 10 2013 213 730 A1 or EP 1 693 665 A1, the light source and the detector are normally accommodated in different measuring heads that are mounted on process flanges on diametrically opposed sides of a plant section containing or carrying the process gas to be measured (for example, an exhaust gas line, a container, or chimney). In order for the light source and the detector to not come into contact with the often aggressive, hot and dust-laden process gas they are arranged behind windows. The window closes one end of a purging pipe that connects with its other open end into the gas-carrying plant section and is purged with a purge gas. The purge gas is chosen such that it has no cross-interference effect on each gas component to be measured, i.e., its spectral absorption lines lie outside the absorption lines of the process gas used for the measurement. The purge gas issues from the open ends of the purging pipes located opposite one another, which means that the measuring path for the absorption measurement of the process gas is determined by the gap between the open ends of the two purging pipes.

The higher the purge gas flow rate, the more effectively the windows can be kept free from contaminants from the process gas. In this situation, the purging rates can vary depending on the application in a range from a few liters per minute up to several hundred liters per minute. When cylinder gas is used, however, there are correspondingly high costs associated with a high consumption of purge gas. Thus, for example, nitrogen is often used as a purge gas for the measurement of oxygen. In cases in which ambient air is suitable as the purge gas, variable moisture content levels may result in cross-interference effects with gas components to be measured.

The gas analysis is based on the specific light absorption of the gas component to be measured and the absorption is dependent on the product of the concentration of the gas component and the absorption path or, in the case of low concentrations, is approximately proportional thereto. Consequently, the measurement is interfered with by the purge gas flowing into the measuring path between the purging pipes located opposite one another and partially displacing and mixing with the process gas at that location. In addition, the inflowing purge gas can change parameters, such as pressure, flow and temperature of the process gas, which affect the light absorption. This leads to the result that the effective absorption path (measuring path) in the process gas to be measured does not match the spacing of the open ends of the two purging pipes but may deviate and vary therefrom to an unknown degree.

The measurement error caused by the purging has hitherto been reduced in that a correction factor for the change in the effective measuring path and/or an offset for a possible effect on the concentration of the purge gas was defined for a constant process constellation. This only functions as long as the process and purging conditions (purge gas concentration, pressure, temperature, volume flow rate) are constant.

In the case of the process gas analyzer known from above-mentioned US 2012/0236323 A1, the purging pipes are separated briefly from the purge gas feed system via a switchable valve and subsequently completely filled with process gas by using a pump or a fan to introduce the process gas into the purging pipes instead of the purge gas or to extract purge gas present in the purging pipes and to replace it with the process gas flowing afterwards. The effective absorption path (measuring path) relevant to the determination of the concentration of the gas component to be measured is determined by the fact that the known distance between light source and detector is multiplied by the ratio of each absorption detected when the purging pipes are filled the one time with the purge gas and the other time with the process gas. Here, the effect of the absorption caused by the purge gas on the measurement is not taken into consideration. The process gas comes into contact with the windows protecting the light source and the detector. The operation of filling the purging pipes with the process gas and subsequently refilling with the purge gas can be performed repeatedly if required, but this does interrupt the current measurement each time.

From EP 1 693 665 A1, it is known to compensate for the effect of the absorption caused by the purge gas on the analysis of the process gas by the fact that after flowing through the purging pipes the purge gas is withdrawn from the pipes and analyzed in a separate measurement channel. The result of the purge gas analysis is subtracted from the result of the process gas analysis. For the separate measurement channel, one part of the light generated for the analysis of the process gas is branched off and, after irradiation of a measuring cuvette through which the collected purge gas is passed, is separately detected. The design effort involved is therefore correspondingly great.

SUMMARY OF THE INVENTION

In view of the foregoing, it is therefore an object of the invention to provide a process gas analyzer and method to enable a high degree of compensation for a measurement error caused by purging even in the event of various and changing process conditions and to allow greater freedoms in the choice of the purge gas, which results in a cost saving with respect to operation of the gas process analyzer.

This and other objects and advantages are achieved in accordance with the invention by a process gas analyzer and method for analyzing a process gas carried in a plant section.

In accordance with the invention, periodic modulation of the volume flow rate of the purge gas during the current measurement or analysis is performed without the purging pipes being separated from the purge gas feed system or even being filled with process gas in this situation in the manner known from US 2012/0236323 A1. As a result, the protection of the windows or of other optical components against contaminants from the process gas is maintained uninterrupted. The volume flow rate can be varied step by step, such as in rectangular or a stepwise manner, or continuously, such as in a sinusoidal or triangular manner. Based on changes in the detected absorption caused by the modulation, in other words correlating therewith, the effect of the purge gas on the analysis result is determined and removed from the analysis result. If the volume flow rate is modified step-by-step, the changes in the detected absorption are ascertained and evaluated at each step. If the volume flow rate is modified continuously, the changes in the detected absorption resulting therefrom are preferably ascertained and evaluated frequency selectively at the modulation frequency and/or harmonics of the modulation, for example, by using a lock-in algorithm.

The modulation of the volume flow rate of the purge gas can be effected in a simple manner via a variable-speed fan for the delivery of the purge gas or a controllable regulator valve in the purge gas feed system. Alternatively, a buffer volume that can modified by a controller, such as a piston/cylinder unit, can be provided as part of the purge gas feed system.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

For further explanation of the invention reference is made in the following to the figures of the drawings, in which.

DETAILED DESCRIPTION OF THE EXEMPLARY EMBODIMENTS

Figure 1:
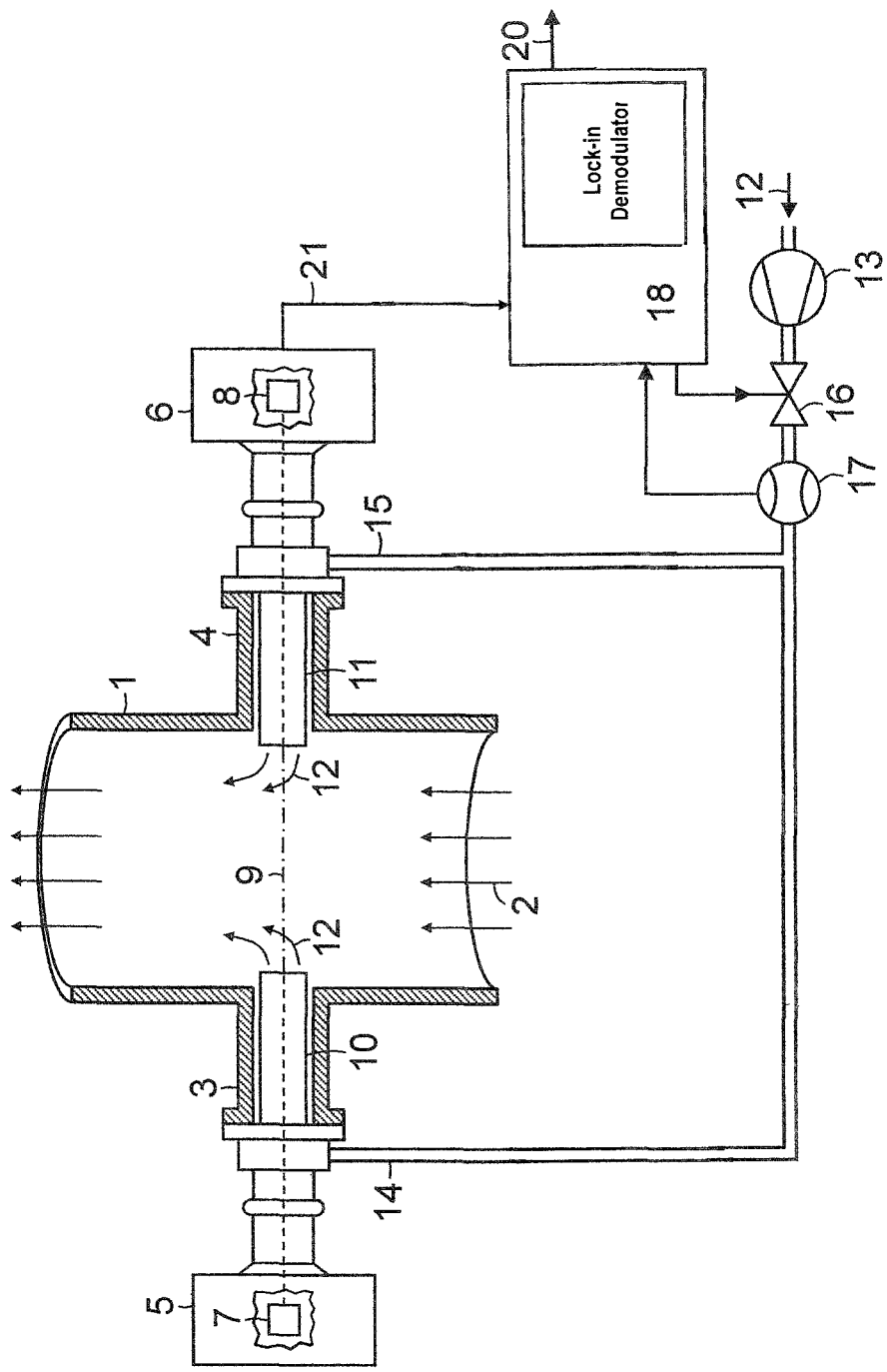
FIG. 1 shows an exemplary embodiment of the process gas analyzer in accordance with the invention.

FIG. 1 shows a schematic illustration of a plant section 1, such as an exhaust gas duct, through which a process gas 2 to be analyzed flows. At two diametrically opposed positions, the plant section 1 has process flanges 3, 4 on which are mounted two measuring heads 5, 6, essentially identical in design, of a process gas analyzer. Each of the two measuring heads 5, 6 contains an optoelectronic element 7, 8 that, in the one case, is a light source 7, such as a laser diode, and in the other case is a detector 8, such as a photodetector. The light 9 generated by the light source 7 is directed through the plant section 1 through which the process gas 2 passes and subsequently strikes the detector 8. The optoelectronic elements 7, 8 are separated by means of windows (not shown) from the interior of the plant section 1 and thereby from the process gas 2, where two purging pipes 10, 11 are provided between the windows and the interior of the plant section 1, which purging pipes 10, 11 are closed at one end by the respective window and connect with their other open end into the interior of the plant section 1. The purging pipes 10, 11 through which the light 9 passes are purged by a purge gas 12 that is driven by a fan 13 and introduced by way of purge gas feeds 14, 15 in each case in the vicinity of the window into the purging pipes 10, 11 and leaves the latter at their open ends. A controllable regulator valve 16 and a flow meter 17 are arranged in the common purge gas feed system. Alternatively, a controllable regulator valve and a flow meter can be present in each of the two purge gas feeds 14, 15. A separate fan can also be provided for each of the two purge gas feeds 14, 15.

Figure 2:
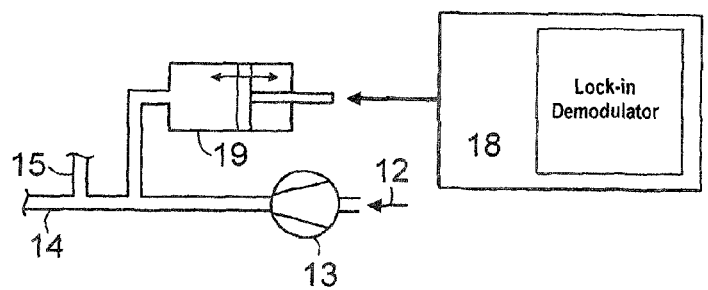
FIG. 2 shows a detail from FIG. 1 with a modifiable buffer volume for modulating the volume flow rate of the purge gas.

FIG. 2 shows a further example in which a buffer volume 19 that can modified by a controller, here a piston/cylinder unit, is present downstream of the fan 13 as part of the purge gas feed system. The volume flow rate of the purge gas 12 towards the purging pipes 10, 11 is modulated by periodic variation of the buffer volume.

Returning to FIG. 1, an evaluation unit 18 that evaluates the wavelength-specific absorption of the light 9 in the process gas 2 to produce an analysis result 20 is arranged downstream of the detector 8. The gas analyzer in question is typically a laser spectrometer, where as known, for example, from DE 10 2012 223 874 B3, the wavelength of the generated light 9 is tuned to a specific absorption line of a gas component of the process gas 2 to be measured and the absorption line is thereby sensed periodically in a wavelength-dependent manner. During the comparatively slow sensing of the absorption line, it is additionally possible to sinusoidally modulate the wavelength of the light at a high frequency and low amplitude. The measurement signal 21 generated by the detector 8 is evaluated directly or after demodulation in the case of an n-th harmonic of the modulation frequency. The evaluation is performed, for example, by fitting the Lorentz profile of an ideal absorption line or the n-th derivative thereof to the curve of the (demodulated where applicable) measurement signal. From the obtained measurement result, the concentration of the gas component to be measured is finally determined as the analysis result 20.

In order to minimize the effect of the purge gas 12 on the analysis result 20, as will be explained in detail in the following with reference to an example, the volume flow rate of the purge gas 12 is modulated with the aid of the regulator valve 16 or alternatively of the fan 13. The modulation is controlled by the evaluation unit 18 which regulates the degree of modulation to a predetermined percentage value on the basis of the measured flow.

The wavelength-dependent decrease in intensity of light 9 on the path from the light source 7 to the detector 8 is described by the Beer-Lambert law:

$$I = I_0 \cdot \exp(-\sigma_{MG} \cdot l_{MG} \cdot c_{MG} - \sigma_{SG} \cdot l_{SG} \cdot c_{SG}), \quad \text{Eq. 1}$$

where at the position (wavelength) of the absorption line of interest of the component to be measured (sample gas):

I is the detected light intensity,

I0 is the initial intensity of the light emitted by the light source 7, $\sigma_{MG}$ is the absorption coefficient of the sample gas, lMG is the measuring path in the process gas, cMG is the concentration of the sample gas, $\sigma_{SG}$ is the absorption coefficient of the purge gas, lSG is the absorption path purged by the purge gas and cSG is the concentration of the purge gas.

With the total absorption path I0=lMG+lSG this gives:

$$I = I_0 \cdot \exp(-\sigma_{MG} \cdot (l_0 - l_{SG}) \cdot c_{MB} - \sigma_{SG} \cdot l_{SG} \cdot c_{SG}). \quad \text{Eq. 2}$$

In the case of a sinusoidal modulation of the purge gas flow the absorption path lSG purged by the purge gas changes accordingly:

$$l_{SG}=l_{SG0}\cdot(1+M\cdot\sin 2\pi ft),\qquad\text{Eq. 3}$$

where M (0<M<1) is the normalized amplitude and f is the frequency of the modulation.

Accordingly the following results for the detected light intensity:

$$I=I_0\cdot\exp(-\sigma_{MB}\cdot l_0\cdot c_{MG}+(\sigma_{MG}\cdot c_{MG}-\sigma_{SG}\cdot c_{SG})\cdot l_{SG0}+(\sigma_{MB}\cdot c_{MB}-\sigma_{SG}\cdot c_{SG})\cdot l_{SG0}\cdot M\cdot\sin 2\pi ft).\qquad\text{Eq. 4}$$

For the purpose of computational simplification, the extinction or absorbance based on the natural logarithm is used in the following:

$$E=-\ln\frac{I}{I_0}=\acute{o}_{MG}\cdot l_0\cdot c_{MG}-(\sigma_{MG}\cdot c_{MG}-\sigma_{SG}\cdot c_{SG})\cdot l_{SG0}-\qquad\text{Eq. 5}$$
$$(\sigma_{MG}\cdot c_{MG}-\sigma_{SG}\cdot c_{SG})\cdot l_{SG0}\cdot M\cdot\sin 2\pi ft.$$

The detected extinction E thus has an alternating component having the amplitude AF in addition to a direct component:

$$AF=(\sigma_{MG}\cdot c_{MG}-\sigma_{SG}\cdot c_{SG})\cdot l_{SG0}\cdot M.\qquad\text{Eq. 6}$$

The equation for the detected extinction E can thereby be rewritten as follows:

$$E=\sigma_{MG}\cdot l_0\cdot c_{MG}-\frac{AF}{M}-AF\cdot\sin 2\pi ft.\qquad\text{Eq. 7}$$

The detected extinction E defined in Eq. 7 therefore consists of a first direct component $\sigma MG\cdot I0\cdot cMG$ unaffected by the purge gas, a second direct component AF/M affected by the purge gas and the alternating component having the amplitude AF.

If the volume flow rate of the purge gas 12 is varied by a predetermined low percentage, such as by 10%, the absorption path lSG purged by the purge gas will also change by a sufficiently close approximation of the same percentage, i.e., the normalized amplitude M will have the value 0.1. The amplitude AF of the alternating component can be ascertained directly by evaluating the extinction E at the modulation frequency f. As a result, the second direct component AF/M mentioned above is also known, here AF/M=AF/0.1=10·AF. Finally, the total absorption path l0 and the absorption coefficient σMG of the sample gas are also known variables, which means that the concentration cMG of the sample gas can be determined from the detected extinction E or of the detected light intensity I free from effects of the purge gas 12.

Figure 3:
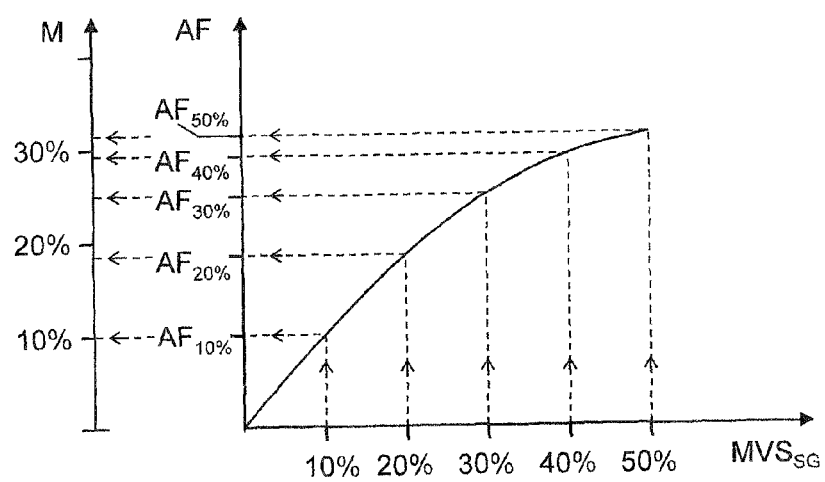
FIG. 3 shows a graphical plot of an exemplary calibration of the process gas analyzer in accordance with the invention.

In the case of greater changes in the volume flow rate of the purge gas 12, the absorption path lSG purged by the purge gas will not change in a linear manner, i.e., not by the same percentage. In this case, the normalized amplitude M at which the absorption path lSG purged by the purge gas changes is ascertained in the context of a "one-off" calibration depending on changes of differing magnitudes in the volume flow rate of the purge gas 12. As illustrated by FIG. 3, to this end, given constant process conditions, the associated amplitude values AF10%, AF20%, . . . AF50% of the alternating component AF of the detected extinction E can be ascertained for various normalized modulation amplitudes MVSSG of the purge gas flow, here for example MVSSG=10%, 20%, . . . 50%. Now M can be determined simply with $$M=\frac{AF\cdot x}{AF_x}\qquad\text{Eq. 8}$$

where x denotes as small a relative modulation amplitude as possible, such that: MVSSG=M=x. If x=10%, when a modulation of the purge gas flow takes place for, example, with MVSSG=50%, then this gives rise to a resulting modulation M of the absorption path lSG purged by the purge gas of:

$$M=\frac{AF_{50\%}\cdot 0.1}{AF_{10\%}}.\qquad\text{Eq. 9}$$

Following the described calibration the method in accordance with the invention can be performed using any desired modulation of the volume flow rate of the purge gas 12, even if the relationship between M and MVSSG is not linear. The purging pipes 10, 11 are not separated from the purge gas feed system. As a result, this ensures that even in the case of a modulation of 100% purge gas 12 is always present in the purging pipes 10, 11 to protect the windows or other optical components.

Although changing process conditions, such as pressure, temperature or volume flow rate of the process gas 2 in the plant section 1, affect the absorption path lSG purged by the purge gas 12, they are however largely compensated for by the method in accordance with the invention. If, for example, the pressure increases in the plant section 1, then the absorption path lSG purged by the purge gas is reduced, where in a first approximation the modulation-dependent change in lSG also changes to the same extent and M thus remains constant.

As already mentioned, the volume flow rate of the purge gas 12 can be modulated in almost any manner to subsequently determine the effect of the purge gas 12 on the analysis result 20 based on the variations in the detected absorption caused by the modulation and calculate the effect from the analysis result 20. For example, a rectangular modulation of the volume flow rate of the purge gas 12 causes the absorption path lSG purged by the purge gas 12 to periodically switch between the values lSG1=lSG0 and lSG2=lSG0·(1+M). Accordingly, two values E1 and E2 for the detected extinction E are obtained in each modulation period:

$$E1=\sigma_{MG}\cdot l_0\cdot c_{MG}-(\sigma_{MG}\cdot c_{MG}-\sigma_{SG}\cdot c_{SG})\cdot l_{SG0}\qquad\text{Eq. 10}$$

and $$E2=\sigma_{MG}\cdot l_0\cdot c_{MG}-(\sigma_{MG}\cdot c_{MG}-\sigma_{SG}\cdot c_{SG})\cdot l_{SG0}-(\sigma_{MB}\cdot c_{MG}-\sigma_{SB}\cdot c_{SG})\cdot l_{SG0}\cdot M.\qquad\text{Eq. 11}$$

AF can be determined from the difference of the values E1 and E2:

$$E1-E2=AF=(\sigma_{MG}\cdot c_{MG}-\sigma_{SG}\cdot c_{SG})\cdot l_{SG0}\cdot M,\qquad\text{Eq. 12}$$

where the following applies to the value E1:

$$E1=\sigma_{MG}\cdot l_0\cdot c_{MG}-\frac{AF}{M}\qquad\text{Eq. 13}$$

and finally to the concentration cMG of the sample gas:

$$c_{MG} = \frac{1}{\sigma_{MG} \cdot l_0} \cdot \left(E1 + \frac{AF}{M}\right) = \frac{1}{\sigma_{MG} \cdot l_0} \cdot \left(E1 + \frac{E1 - E2}{M}\right). \quad \text{Eq. 14}$$

As previously mentioned above, when there is a small modulation of the volume flow rate of the purge gas 12 of, for example, 10% the absorption path lSG purged by the purge gas 12 changes by the same percentage, i.e., M=0.1. In this case, the following results for the concentration cMG of the sample gas:

$$c_{MG} = \frac{1}{\sigma_{MG} \cdot l_0} \cdot (11 \cdot E1 - 10 \cdot E2). \quad \text{Eq. 15}$$

Figure 4:
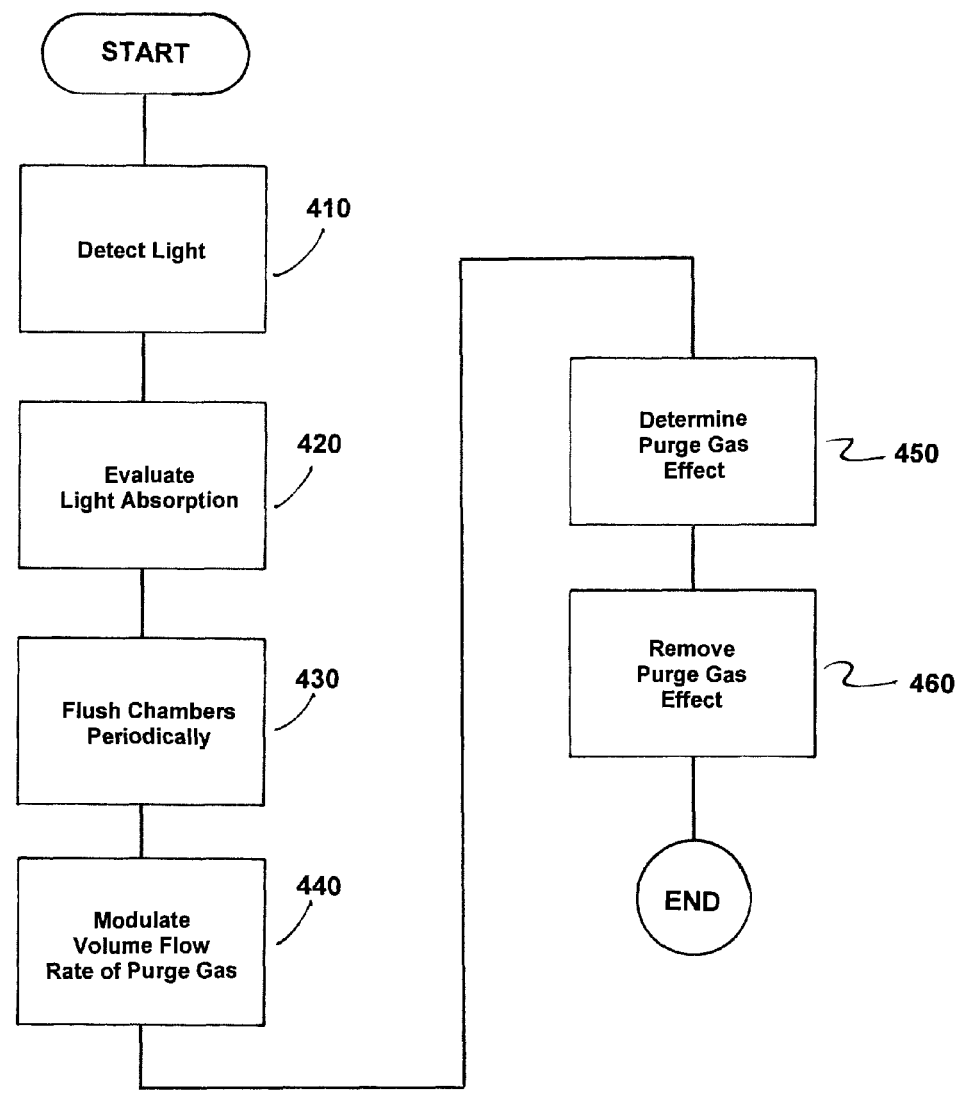
FIG. 4 is a flowchart of the method in accordance with the invention.

FIG. 4 is a flowchart of a method for analyzing a process gas 2 carried in a plant section 1. The method comprises detecting light 9 from a light source 7 via a detector 8 after the light is passed through the process gas 2, as indicated in step 410.

Next, the light is evaluated with respect to absorption in the process gas 2 in an evaluation unit 18 arranged downstream to produce an analysis result 20, as indicated in step 420.

Chambers 10, 11 present between the light source 7 and the plant section 1 and between the detector 8 and the plant section 1 and open towards an interior of the plant section 1 are now flushed with a purge gas 12, as indicated in step 430. Next, the volume flow rate of the purge gas 12 is modulated periodically, as indicated in step 440.

The effect of the purge gas 12 on the analysis result 20, based on changes in the detected absorption caused by the periodic modulation, is now determined, as indicated in step 450. Next, the effect of the purge gas 12 on the analysis result is removed from the analysis result 20, as indicated in step 460.

While there have been shown, described and pointed out fundamental novel features of the invention as applied to a preferred embodiment thereof, it will be understood that various omissions and substitutions and changes in the form and details of the methods described and the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A process gas analyzer for analyzing a process gas carried in a plant section, comprising:
    a detector;
    an evaluation unit arranged downstream of the detector;
    a light source, light from said light source passing through the process gas and being detected by said detector and evaluated with respect to absorption in the process gas in the evaluation unit to produce an analysis result; and
    a purge gas system including a first chamber provided between the light source and the plant section and a second chamber provided between the detector and the plant section, the first and second chambers being open towards an interior of the plant section and being flushed with a purge gas such that the light passes a total absorption path comprising an absorption path purged by the purge gas and a measuring path in the process gas;
    wherein the purge gas system further includes a flow rate modulator for periodic modulation of a volume flow rate of the purge gas provided to the purge gas system such that a resulting modulation of the total absorption path purged by the purge gas is less than 100%; and
    wherein the evaluation unit is configured to determine an effect of the purge gas on the analysis result based on changes in a detected absorption caused by the periodic modulation and to remove said determined effect from the analysis result.

2. The process gas analyzer as claimed in claim 1, wherein the evaluation unit contains a lock-in demodulator which ascertains an amplitude of changes in the detected absorption at a modulation frequency of the volume flow rate.

3. The process gas analyzer as claimed in claim 2, wherein the flow rate modulator for modulating the volume flow rate of the purge gas comprises a variable-speed fan.

4. The process gas analyzer as claimed in claim 2, wherein the flow rate modulator for modulating the volume flow rate of the purge gas comprises a controllable regulator valve arranged in a purge gas feed system which feeds each respective chamber.

5. The process gas analyzer as claimed in claim 2, wherein the flow rate modulator for modulating the volume flow rate of the purge gas comprises a buffer volume which is modifiable via a controller arranged in the purge gas feed system which feeds each respective chamber.

6. The process gas analyzer as claimed in claim 1, wherein the flow rate modulator for modulating the volume flow rate of the purge gas comprises a variable-speed fan.

7. The process gas analyzer as claimed in claim 1, wherein the flow rate modulator for modulating the volume flow rate of the purge gas comprises a controllable regulator valve arranged in a purge gas feed system which feeds each respective chamber.

8. The process gas analyzer as claimed in claim 1, wherein the flow rate modulator for modulating the volume flow rate of the purge gas comprises a buffer volume which is modifiable via a controller arranged in the purge gas feed system which feeds each respective chamber.

9. A method for analyzing a process gas carried in a plant section, comprising:
    detecting light from a light source via a detector after said light is passed through the process gas;
    evaluating said light with respect to absorption in the process gas in an evaluation unit arranged downstream to produce an analysis result;
    flushing chambers included in a purge gas system with a purge gas such that the light passes a total absorption path comprising an absorption path purged by the purge gas and a measuring path in the process gas, the chambers being open towards an interior of the plant section and present between the light source and the plant section and between the detector and the plant section;
    modulating periodically, by a flow rate modulator, a volume flow rate of the purge gas provided to the purge gas system;

determining, by the flow rate modulator, based on changes in the detected absorption caused by said periodic modulation gas, an effect of the purge gas on the analysis result; and removing by the evaluation unit, said effect of the purge gas on the analysis result from the analysis result based on the changes in the detected absorption caused by said periodic modulation;

wherein the purge gas system further includes the flow rate modulator for periodic modulation of the volume flow rate of the purge gas provided to the purge gas system such that a resulting modulation of the total absorption path purged by the purge gas is less than 100%.

10. The method as claimed in claim 9, wherein amplitude of the changes in the detected absorption is ascertained at the modulation frequency of the volume flow rate via lock-in demodulation.

11. The method as claimed in claim 10, wherein the flow rate modulator which modulates the volume flow rate of the purge gas comprises a variable-speed fan.

12. The method as claimed in claim 10, wherein the volume flow rate of the purge gas is modulated via a controllable regulator valve arranged in a purge gas feed system.

13. The method as claimed in claim 10, wherein the volume flow rate of the purge gas is modulated via a modifiable buffer volume arranged in a purge gas feed system.

14. The method as claimed in claim 9, wherein the flow rate modulator which modulates the volume flow rate of the purge gas comprises a variable-speed fan.

15. The method as claimed in claim 9, wherein the flow rate modulator which modulates the volume flow rate of the purge gas comprises a controllable regulator valve arranged in a purge gas feed system.

16. The method as claimed in claim 9, wherein the volume flow rate of the purge gas is modulated via a modifiable buffer volume arranged in a purge gas feed system.

* * * * *